(12) United States Patent
El-Hajal et al.

(10) Patent No.: US 10,831,042 B2
(45) Date of Patent: Nov. 10, 2020

(54) SYSTEM AND METHOD FOR OBTAINING AND UTILIZING MEASUREMENTS TO ENABLE CUSTOMIZED EYEWEAR TO BE PURCHASED ONLINE

(71) Applicant: Optikam Tech, Inc., Montreal (CA)

(72) Inventors: Bassem El-Hajal, Montreal (CA); Marco Lancione, Montreal (CA); Piotr Szymborski, Montreal (CA); Luc Jalbert, Montreal (CA)

(73) Assignee: Optikam Tech, Inc., Montreal (CA)

( * ) Notice: Subject to any disclaimer, the term of this patent is extended or adjusted under 35 U.S.C. 154(b) by 153 days.

(21) Appl. No.: 15/970,546

(22) Filed: May 3, 2018

(65) Prior Publication Data

US 2019/0339546 A1 Nov. 7, 2019

(51) Int. Cl.
| | | |
|---|---|---|
| A61B 3/10 | (2006.01) |
| G02C 13/00 | (2006.01) |
| A61B 3/18 | (2006.01) |
| G02C 7/02 | (2006.01) |

(52) U.S. Cl.
CPC ............... *G02C 13/005* (2013.01); *A61B 3/18* (2013.01); *G02C 7/027* (2013.01)

(58) Field of Classification Search
CPC ..... A61B 3/0025; A61B 3/0033; A61B 3/111; A61B 3/18
USPC ........ 351/200, 204–206, 209–211, 221–223, 351/243–246
See application file for complete search history.

(56) References Cited

U.S. PATENT DOCUMENTS

| | | |
|---|---|---|
| 5,280,570 A | 1/1994 | Jordan |
| 6,761,453 B2 | 7/2004 | Wilson |
| 6,792,401 B1 | 9/2004 | Nigro et al. |
| 9,086,582 B1 * | 7/2015 | Barton .................... A61B 3/111 |
| 9,703,123 B2 | 7/2017 | Fonte et al. |
| 9,817,248 B2 | 11/2017 | Yang et al. |
| 9,842,370 B1 | 12/2017 | Ingles et al. |
| 2004/0004633 A1 | 1/2004 | Perry et al. |
| 2004/0189935 A1 | 9/2004 | Warden et al. |
| 2008/0198328 A1 | 8/2008 | Seriani et al. |
| 2014/0257839 A1 | 9/2014 | Suter et al. |
| 2014/0268058 A1 | 9/2014 | Balter |
| 2015/0019389 A1 * | 1/2015 | Leonard ............... A61B 3/0083 705/27.2 |

* cited by examiner

*Primary Examiner* — Brandi N Thomas
(74) *Attorney, Agent, or Firm* — LaMarte & Associates, P.C.

(57) ABSTRACT

A system and method for determining the measurements needed to correctly fabricate prescription eyewear for an individual who is purchasing the eyewear. The individual is provided with an initial set of frames. The initial set of frames is fitted to the requirements of the individual to obtain a fitted frame. An eye exam is also conducted to obtain a proper lens prescription for the fitted frames. The individual is imaged while the fitted frames are being worn. This creates reference images. At some point, the individual may select a subsequent set of frames. Once the subsequent set of frames is selected, a retailer recalls the reference images and obtains fitting measurements from the reference images. The online retailer can also recall the lens prescription for the initial fitted frames. Utilizing the fitting measurements, the retailer can custom fit the subsequent set of frames.

10 Claims, 6 Drawing Sheets

SYSTEM AND METHOD FOR OBTAINING AND UTILIZING MEASUREMENTS TO ENABLE CUSTOMIZED EYEWEAR TO BE PURCHASED ONLINE

BACKGROUND OF THE INVENTION

1. Field of the Invention

In general, the present invention relates to systems and methods that enable a person to purchase customized eyewear online. More particularly, the present invention relates to systems and methods that enable a provider to utilize stored information to create fitted prescription eyewear without the presence of the wearer.

2. Prior Art Description

When a person gets a prescription for eyeglass lenses and selects a set of eyeglass frames, those lenses are not taken out of the box, set into the frames, and handed to the customer. Rather, the lenses must be fabricated in a manner that takes into account the style of the selected eyeglass frames and the anatomical features of the person who will wear the eyeglass frames. When prescription lenses are fitted for a particular set of frames and for a particular person, several measurements must be made in order to ensure that the prescription lenses are fabricated properly. Many of the measurements depend solely upon the style and model of the eyeglass frames being considered. Other measurements depend upon the anatomy of the person being fitted. Still other measurements depend upon how the eyeglass frames sit upon the face when being worn in a normal manner. For instance, the distance between a person's eyes varies from person to person. Furthermore, the shape and slant of a person's nose varies from person to person. The size and slant of the nose determines how far down the face a set of eyeglass frames will come to rest in front of the eyes. This determines what portions of the lenses are positioned in front of the pupils when a person looks straightforward. Accordingly, the way the lenses in the frames rest upon the face is a significant variable in how the lenses should be fabricated.

In addition to a person's facial anatomy, the position of the head and the posture of the body also have significant effects on the proper fitting of eyeglasses. Few people have a fully erect posture and view their environment by only looking straight ahead. Rather, most people have a slight slouch. Furthermore, most people look slightly downward as they walk or when they sit. Some people also have a tendency to tilt their head to one side or another as they drive or read. Each one of these head positions causes a person to look through a slightly different section of the lenses in a set of eyeglasses.

In order to properly create the lenses for a selected set of frames, many measurements must be taken. Traditionally, the measurements are taken by placing selected eyeglass frames onto the wearer. An optician or other technician then uses a variety of instruments to quantify the measurement variables needed to properly create prescription lenses for those eyeglass frames.

In the prior art, there are systems that enable a person to purchase prescription eyewear without having to travel to an optician. Some prior art systems use virtual 3D models of both the user's face and of the eyeglass frames. The virtual eyeglass frames are then superimposed over the virtual face to access aesthetics and fit. Such prior art systems are exemplified by U.S. Pat. No. 9,817,248 to Yang. These prior art systems are good for viewing the way eyeglasses look on a person. However, such systems simply position virtual eyeglasses in front of a virtual face. There are no adjustments for how gravity causes the eyeglasses rest on the nose or how a person orient's his/her head. Accordingly, any measurements that are obtained from such virtual model systems are only estimates and are not completely accurate.

In U.S. Patent Application Publication No. 2014/0257839 to Suter, a prior art system is shown that enables a person to buy prescription eyewear online. The system takes an existing prescription for eyewear and adapts that prescription to any set of eyeglass frames that are selected online by the user. Although the prescription for the lenses may be known, there are no measurements used that are based upon the anatomy of the face. Accordingly, if the style of the eyeglass frame rests lower on the nose than expected, then the prescription will be flawed, and the eyeglasses will not be as effective as they should be.

A need therefore exists for a system and method that can be used to determine the measurements needed to accurately fabricate prescription eyewear selected by a user online, wherein the user is not directly being fitted for the eyewear selected. This need is met by the present invention as described and claimed below.

SUMMARY OF THE INVENTION

The present invention is a system and method for determining the measurements needed to correctly fabricate prescription eyewear for an individual who is purchasing the eyewear without a fitting or eye exam. In accordance with the present invention, the individual is provided with an initial set of frames. The initial set of frames is fitted to the requirements of the individual to obtain a fitted frame. An eye exam may be conducted to obtain a proper lens prescription for the fitted frame. Otherwise, prescription data can be obtained from some other source, such as the user's prior eyewear. The individual is imaged while the fitted frame is being worn. This creates reference images.

At some point, the individual may select a subsequent set of frames. This may be done online where a fitting cannot be conducted. Once the subsequent set of frames is selected from an online retailer, the online retailer recalls the reference images and obtains fitting measurements from the reference images. The online retailer can also recall the lens prescription for the initial fitted frames.

Utilizing the fitting measurements, the online retailer can custom fit the subsequent set of frames. The fitting measurements can also be used to adjust the lens prescription to the subsequent set of frames. The result is a new set of eyewear that is custom fit to the physical and optical needs of an individual.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

The present invention is a system and method that is used to purchase custom fit eyewear online or in some other manner where the purchaser is unavailable for a fitting. The system and method can be used to purchase many different types of customize eyewear, such as eyeglasses, sunglasses, and safety glasses. However, only one exemplary embodiment for the purchase of eyeglasses is illustrated and described. This exemplary embodiment is intended to represent most all models and styles of prescription eyewear. Accordingly, the specifics of the exemplary eyeglasses should not be considered a limitation in the interpretation of the appended claims.

Figure 1:
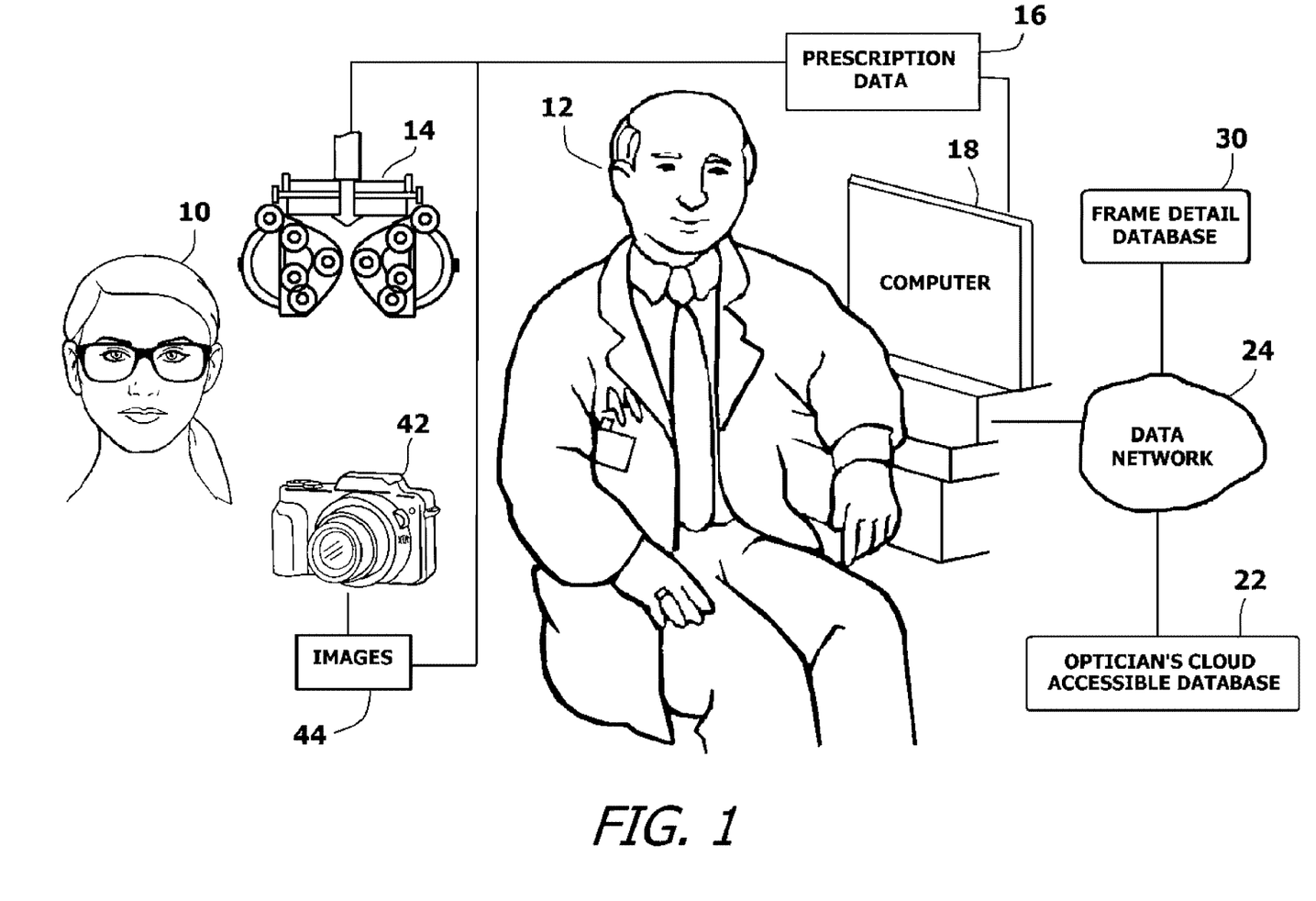
FIG. 1 is a schematic that illustrates the requirements for obtaining reference images and prescription data for an individual.
Figure 2:
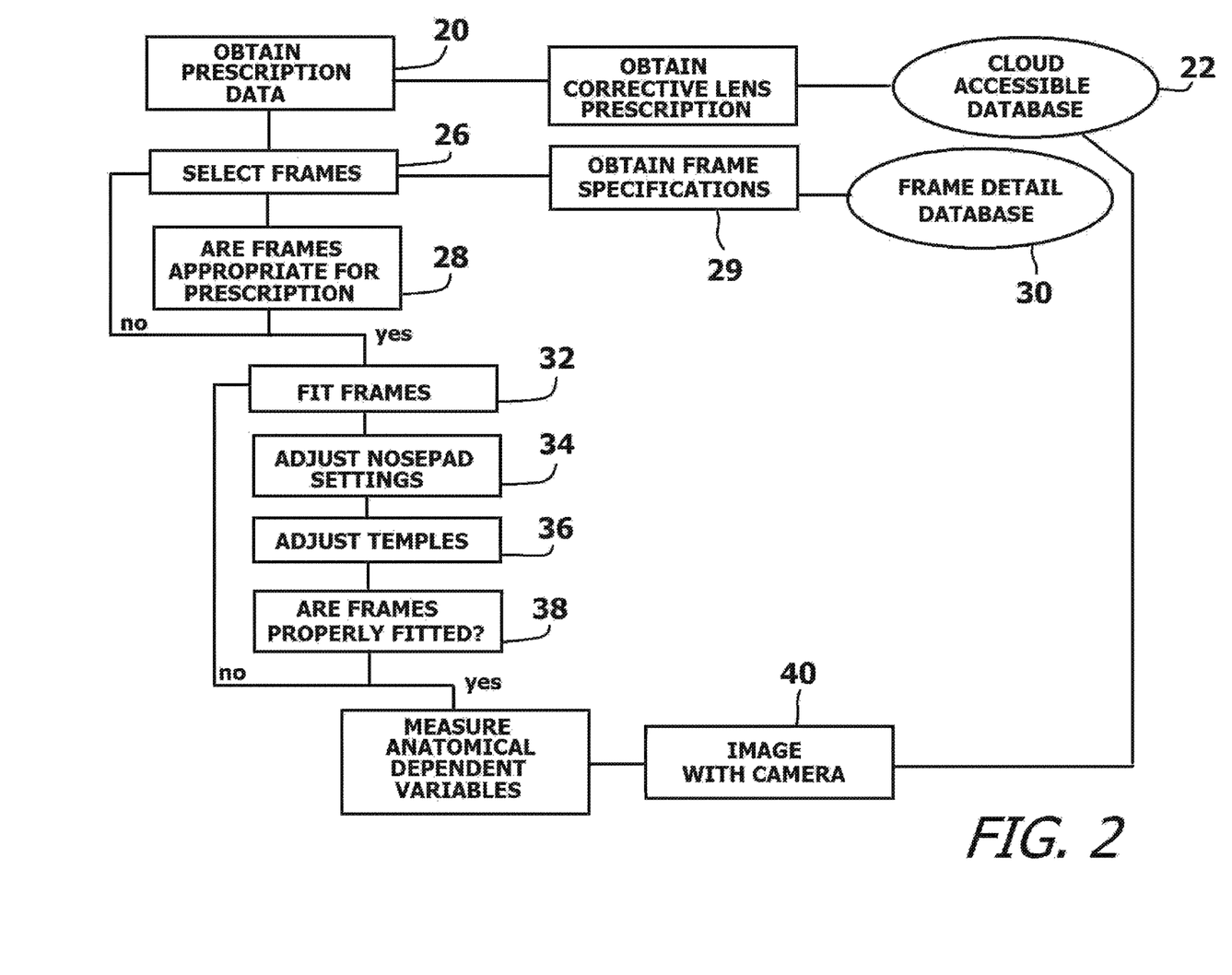
FIG. 2 is a block diagram illustrating the methodology used to obtain reference images and prescription data for an individual.

Referring to FIG. 1, in conjunction with FIG. 2, it will be understood that at some point in time, a system user 10 who needs prescription eyewear must visit an optician 12 or similar technician in order to obtain a corrective lens prescription. Typically, an eye exam is conducted using diagnostic equipment 14, such as a phoropter. The diagnostic information obtained from the eye exam is used to generate prescription data 16. The prescription data 16 is typically stored in the computer system 18 of the optician. This information may be stored on site at the optician's office. However, it is preferred that the prescription data 16 be stored in a cloud accessible database 22 that is accessed through a data network 24, such as the Worldwide Web.

An eye exam need not be performed to use the present invention system. If the eyewear being ordered is prescription eyewear, prescription data 16 is required. The prescription data 16 can be obtained from records of old exams or even by analyzing the current eyewear of the user 10. It will therefore be understood that the prescription data is obtained from some source. See Block 20.

Once the prescription data 16 is obtained from some source, the user 10 selects frames into which prescription lenses are to be mounted. See Block 26. Once the user 10 selects frames, the selected frames are checked to ensure that they are properly sized for the user's head and that the frames can hold the proper prescription lenses. See Block 28. Once the frames are selected and verified, the frame's physical specifications are obtained. See Block 29. These specifications are needed to properly grind and fit the prescription lenses to the selected frames. The frame's physical specifications can be measured from the frame or can be downloaded from a frame detail database 30 provided online by the frame's manufacturer or distributor.

Once the frames are selected, verified and recorded, the frames are fitted to the facial features of the user. See Block 32. This typically involves adjusting the nose pad settings and the temples on the frames. See Block 34 and Block 36. The adjustments to the nose pad settings and the adjustments to the temples both affect how the selected frames rest on the nose and are positioned in front of the eyes.

Once the frames are properly fitted, the user 10 is imaged wearing the fitted frames. See Block 38 and Block 40. The user is imaged using a camera 42. The imaging can be performed in an optician's office or at any other location, provided the correct imaging protocols are followed. The proper protocols require that images are taken with the user 10 holding their head in a normal relaxed orientation and with the frames positioned in a normal comfortable position. The images 44 are downloaded to a computer system 18 and are stored in the cloud accessible database 22.

In addition to being imaged, the optician 12, the user 10, or another informed individual may take measurements of anatomical dependent variables. See Block 46. The anatomical dependent variables are physically measured variables, such as pupil distance, pupil height, pantoscopic tilt angle, and rear vertex distance that depend, in part, upon the anatomy of the user's face. The anatomical dependent variables are important in determining the final shape of the lenses to be ground.

Figure 3:
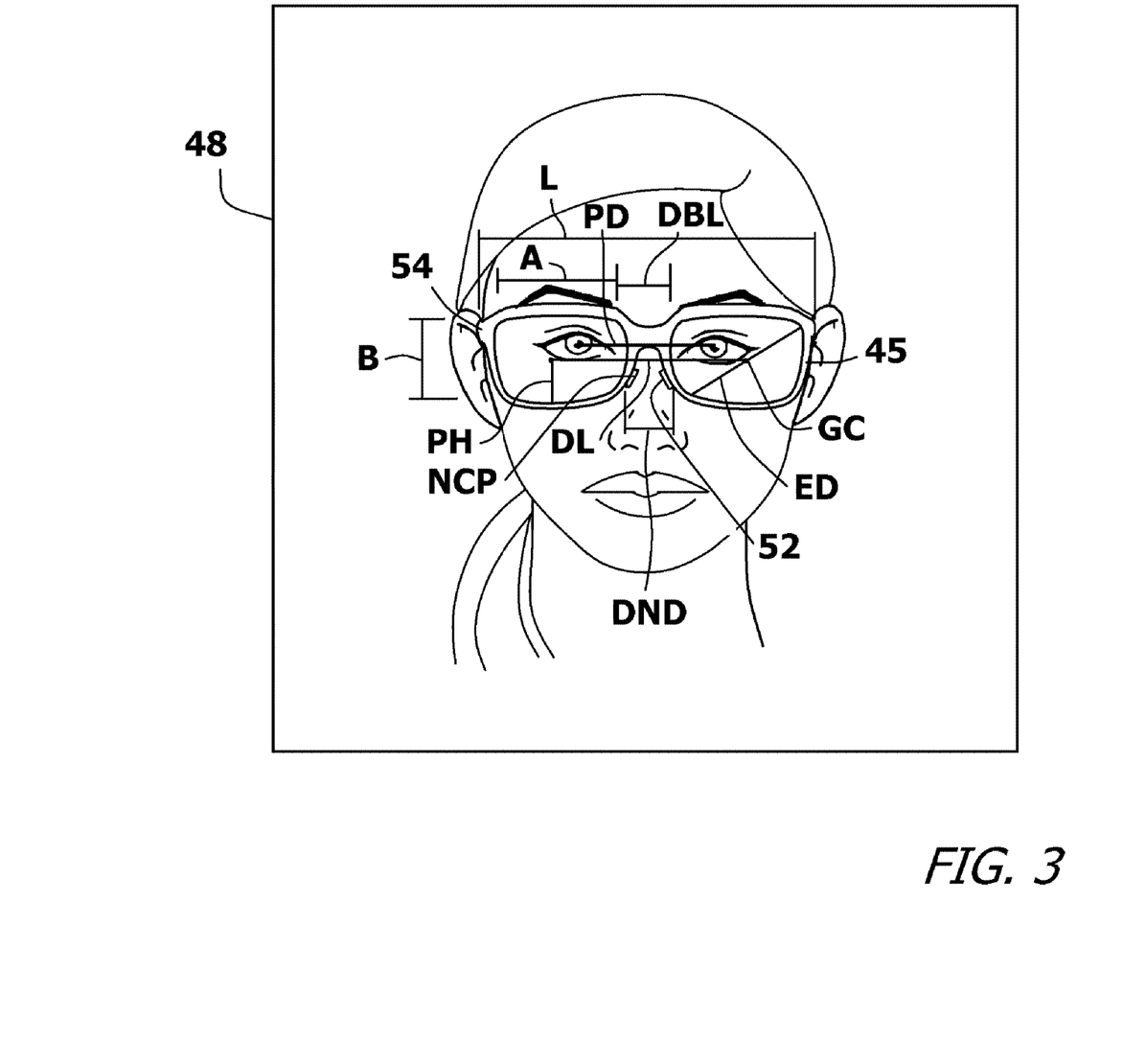
FIG. 3 is a front image of an individual wearing eyeglass frames, wherein the image indicates some of the variables needed to be known for the proper fabrication of prescription eyewear.
Figure 4:
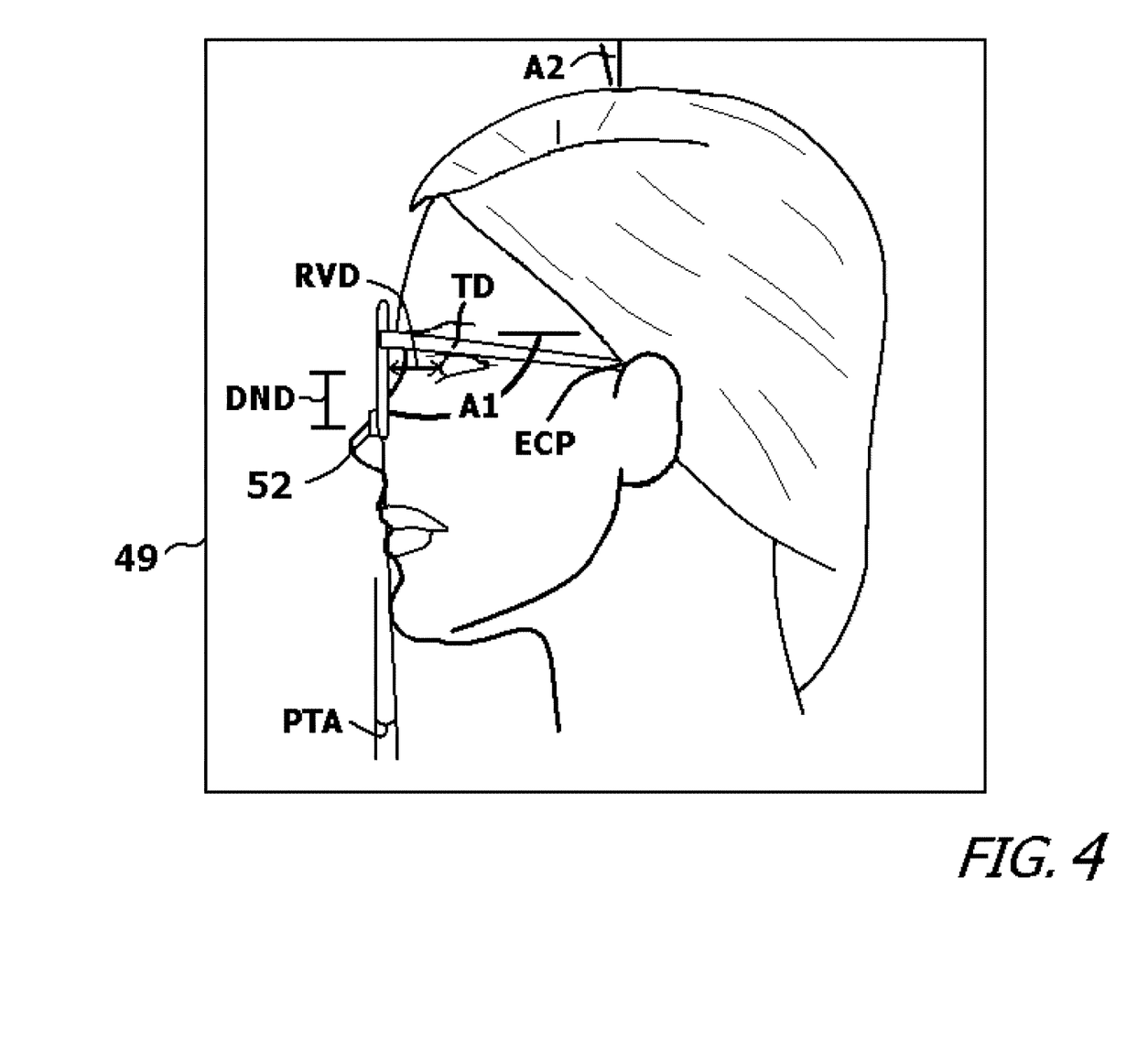
FIG. 4 is a side view of an individual wearing eyeglass frames and indicating some of the variables needed for the proper fabrication of prescription eyewear.

Referring to FIG. 3 in conjunction with FIG. 4, it can be seen that by using the images 44 of the user 10 with the fitted frames 45, a variety of the measurements can be determined directly from the images. The images 44 include a front image 46 and at least one secondary image. The secondary image can be a side image, a top image or a perspective image, provided the secondary image clearly shows the distance between the fitted frames 45 and the facial features of the user 10. The preferred secondary image is a side image 49, wherein the side image 49 is being used as the illustrated example of FIG. 4. In order to obtain measurements from images 44, a measurement scale for the images 44 needs to be established. A measurement scale can be established by knowing the dimensions of at least one aspect of the fitted frames 45 being imaged. As previously explained, the dimensions of the fitted frames 45 are known and are accessible via the Worldwide Web. Accordingly, the images 44 of the user 10 contain a frame identifier field 50 that identifies the manufacturer, make and model of the fitted frames 45 in the images 44. By accessing the dimensions of the fitted frames 45 in the images 44, the images 44 are readily scaled.

In the images 44, many measurements are known or are easily discernable via a computer search. These measurements are the physical dimensions for the make and model of the fitted frames 45 in the images 44. Using the images 44 and the scale provided by the known dimensions of the fitted frames 45, many other measurements can be made that reference the anatomy of the eyes and face. The measurement data is sufficient to provide an optician or other technician with all the information needed to create custom fitted eyewear with a different make and model of frames. Collectively, all the major variables that are needed to properly fabricate custom eyewear are present in Table 1, below.

TABLE 1

| Frame Specifications |
| --- |
| A—Lens Length |
| B—Lens Height |
| ED—Effective Diameter |
| GC—Geometric Centers |
| DL—Datum Line |
| L—Frame Length |
| DBL—Distance Between Lenses |
| TD—Temple Dimensions |
| Anatomical Dependent Variables |

TABLE 1-continued

PH—Pupil Height
PD—Pupil Distance
PTA—Pantoscopic Tilt Angle
RVD—Rear Vertex Distance
DND—Distance between nose pad contact and Datum
DCT—Distance between cheek and temple plane
NCP—Nose Contact Points
ECP—Ear Contact Points FIG. 3 shows the front image 48 of the user 10 wearing fitted frames 45. FIG. 4 is a side image 49 of the same. Referring to Table 1 in conjunction with FIG. 3 and FIG. 4, it will be understood that each model and style of frames has variables that need to be known in order to customize lenses for the frames. Typically, the lens plane associated with a set of fitted frames 45 is at a slight angle relative to the vertical. This tilt angle A1 is sometimes referred to as the "device panto" in the industry. The tilt of the lens plane is also affected by the tilt angle A2 of the person's head. This tilt angle A2 is caused by posture and the way a person holds his/her head.

Within the overall shape of the frames, there are the lens length "A" and the lens height "B". There is the effective diameter "ED" as measured through the geometric center "GC" of each lens. The geometric centers "GC" of both lenses align horizontally on the datum line "DL". The distance between the geometric centers "DBC" is the distance between the geometric centers "GC" in the horizontal plane. The frame length "L" is the distance between the temples in the horizontal plane. The bridge size, or distance between lenses "DBL" is the minimum distance between the left and right lenses 14. The temple dimensions "TD" are the physical dimensions (length, angle and termination) of the temples. The pantoscopic tilt angle "PTA" corresponds to the total tilt of the lens plane. The proper pantoscopic tilt angle "PTA" for an individual is highly dependent upon the natural head posture of that individual. This is because the vertical plane is a constant and any downward tilt of the head directly changes the tilt of the fitted frames 45 relative the vertical plane. As such, the pantoscopic tilt angle "PTA" is the sum of the tilt angle A1 caused by the device panto plus the tilt angle A2 caused by head posture.

Other measurements that depend upon the anatomy of the person wearing the fitted frames 45 include pupil height "PH", pupil distance "PD", and rear vertex distance "RVD". The pupil height "PH" is the measured height of the pupils above the bottom of the lens. The pupil distance "PD" is the distance between pupils in the horizontal plane. The rear vertex distance "RVD" is the gap distance between the pupil and the lens. The fitted frames 45 have nose pads 52. The nose pads 52 contact the nose at the nose contact points "NCP". Likewise, the temples contact the user's ears at temple contact points "TCP". Depending upon the set position of the nose pads 52, the NCP for the nose pads 52 will be at a certain point below the datum line "DL". The distance between the nose pads 52 and datum "DND" is an important measurement obtained from the images 44, as is later explained. Likewise, the fitted frames 45 have temples 54. The user 10 has cheeks. The distance between the cheeks and the plane of the temples "DCT" is an important measurement to prevent the frames 45 and/or lenses from contacting the cheeks when worn.

The pantoscopic tilt angle "PTA", pupil height "PH" and the rear vertex distance "RVD" are measurements that determine the orientation of the lenses in front of the eyes. These variables also show how a person normally orients his/her head when wearing the fitted frames 45. The measurements of Table 1 are readily obtained from images 44 of the fitted frames 45 being worn. Alternately, some of the variables can be measured using prior art measuring devices, such as the prism device disclosed in U.S. Pat. No. 8,857, 986 to Fischer.

Figure 5:
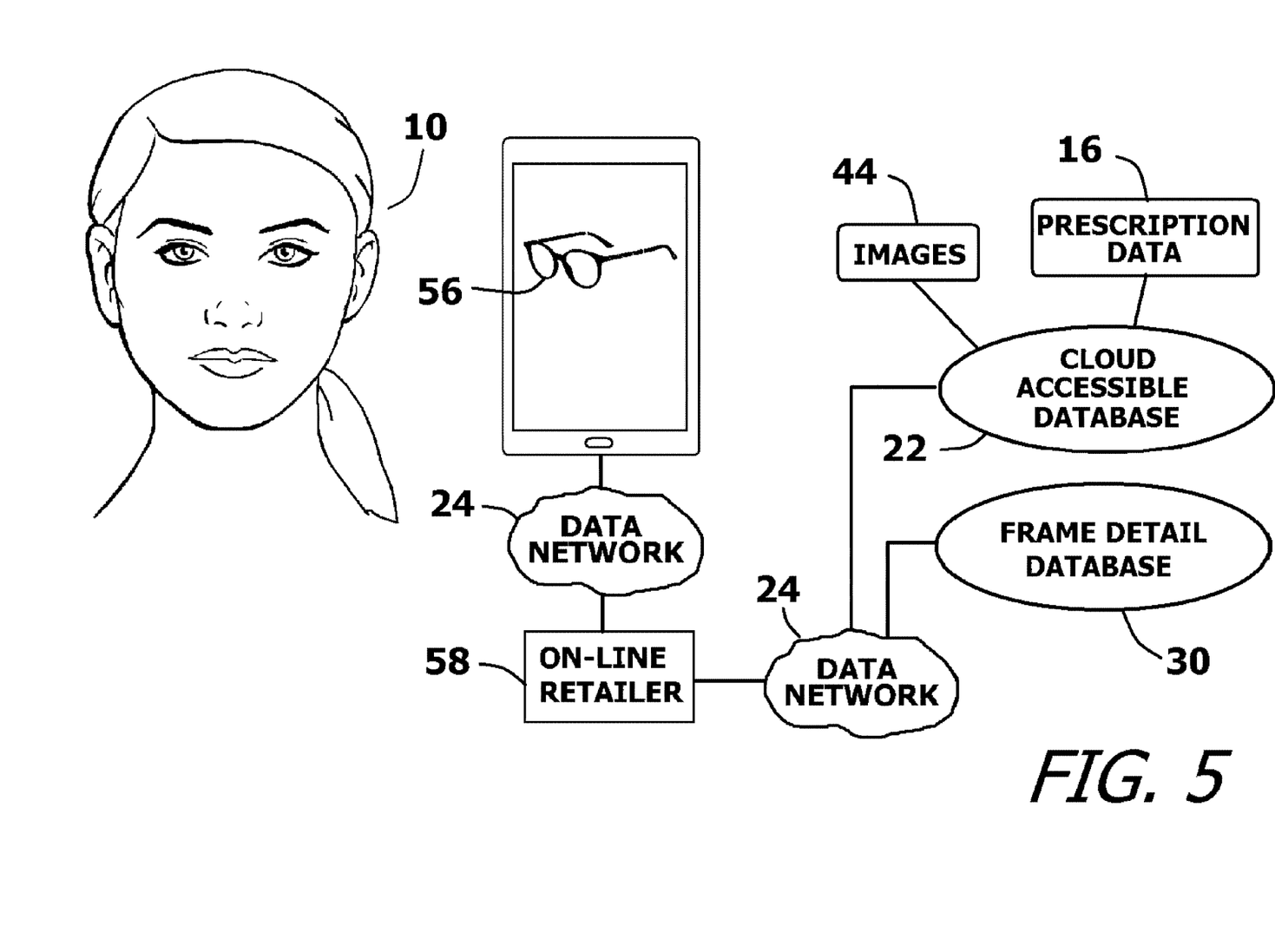
FIG. 5 is a schematic illustrating the online purchase of fitted eyewear by an individual.
Figure 6:
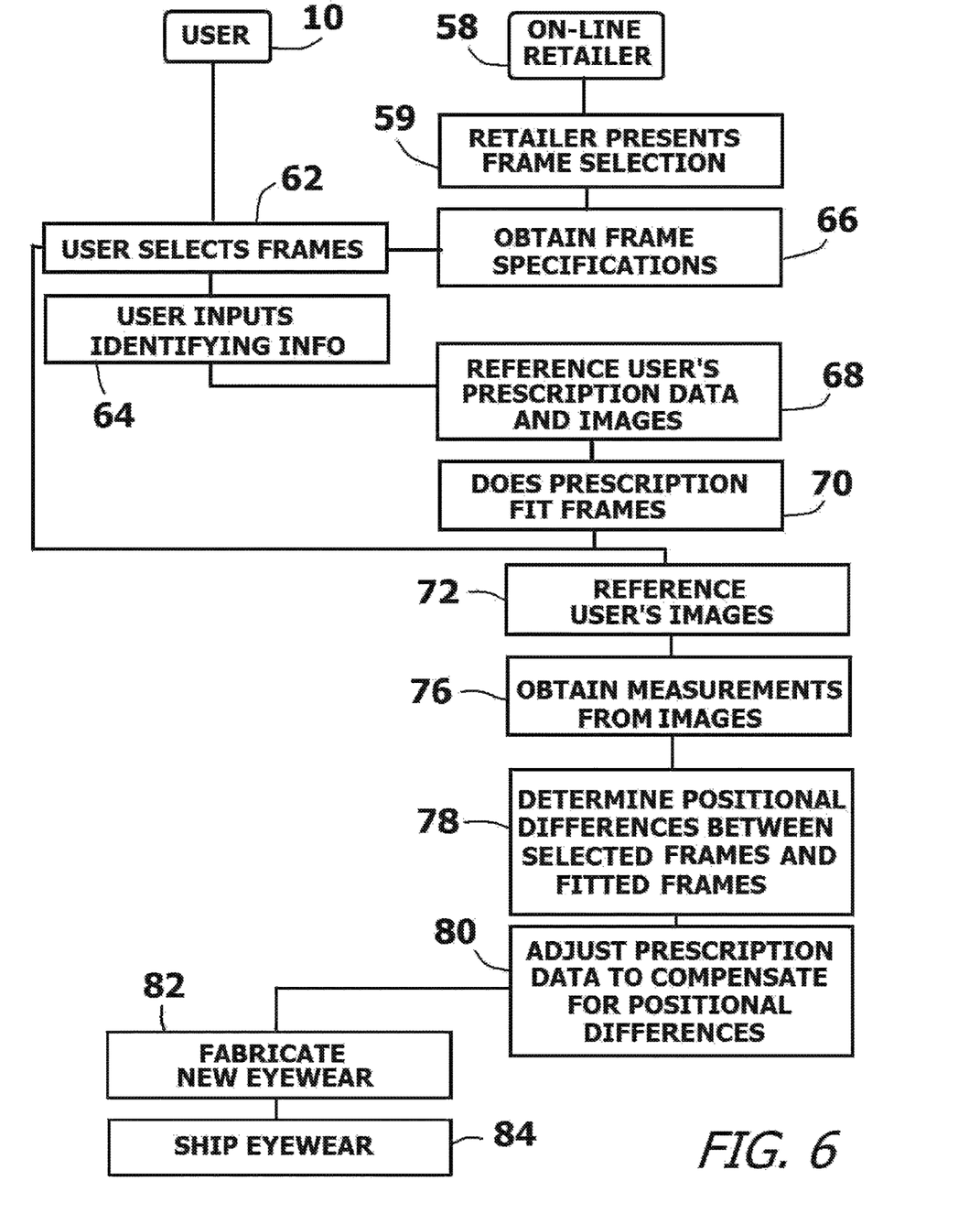
FIG. 6 is block diagram showing the methodology of the present invention system.

Referring to FIG. 5 and FIG. 6, it can be seen that the user 10 may want to purchase new eyewear through a venue where a proper fitting is not possible. For example, the user 10 may find new frames 56 that the user 10 likes from a selection presented by an online retailer 58. See Block 59. The goods of the online retailer 58 are viewed using a computing device 60, such as a laptop or smart phone. The new frames 56 are viewed via data transmission through a data network 24. Accordingly, the user 10 cannot physically touch and try on the selected new frames 56. The user 10 selects the new frames 56 using the computing device 60, See Block 62. If the new frames 56 are to be a part of customized prescription eyewear, then the online retailer 58 needs to fabricate the eyewear to the requirements of the user 10. In order to create a proper fabrication, the online retailer 58 needs information, both about the new frames 56 selected and about the user 10 who selected the frames. Once a user 10 selects the new frames 56 online, the user 10 will be prompted to input information that the online retailer 58 will need to reference relevant data for the user 10. See Block 64.

As indicated by Block 66, the online retailer 58 references the new frames 56 selected by the user 10. Since the selected new frames 56 are part of the online user's inventory, the online retailer 58 may have the physical dimensions of the new frames 56. If not, those dimensions can be downloaded from the frame detail database 30 via the data network 24. Using the same data network 24, the online retailer 58 references the user's records from the cloud accessible database 22. See Block 68. The records contain the prescription data 16 of the user 10 and images 44 of the user wearing properly fitted eyewear. The online retailer 58 then makes a quick determination if the new frames 56 selected by the user 10 are capable of being fabricated with the types of lenses required by the prescription data 16. If no such match is possible, the user 10 is informed of the error and invited to select a different set of frames 56. See Block 70.

Assuming that the selected new frames 56 can be fitted with the lenses required by the prescription data 16, then the online retailer 58 needs anatomical data to obtain values for all the variables listed in Table 1. The online retailer 58 knows the dimensions of the selected new frames 56. What the online retailer 58 does not know is how the new frames 56 will sit on the user's face and how the resting position of the new frames 56 may require modifications to the prescription data 16. In order to find this information, the online retailer 58 references the images 44 from the cloud database 22. See Block 72. The images 44 are used to obtain the needed measurements. See Block 74. From the images 44, the online retailer 58 can measure the distance between the nose pads 52 on the properly fitted eyewear. The online retailer 58 sets the nose pads on the selected new frames 56 to match. Since the nose pad distances are set at the same value, the nose pads should rest upon the user's nose at or near the same point. The datum line is known for the new frames 56. Accordingly, the distance between the datum line and the nose pad position can be determined. The distance between the nose pad level and the datum line is compared between the selected new frames 56 and the prior imaged fitted frames 45. See Block 76. If the distance is the same, the new frames 56 will hold the prescription lenses at the same position in front of the eyes. If there is a difference in the distances, it can be determined that the new frames 56 will hold the lenses either higher on the face or lower on the face, relative to the user's eyes. This differential in position is then used to alter the prescription data 16 so that the pupil height in the prescription data 16 is correct for the new frames 56. See Block 80. Additionally, with the height of the new frames 56 on the face being determined, the online retailer 58 can configure the temples of the new frames 56 to retain the new frames 56 at the proper position. The temples can also be checked against the user's check position to ensure that the selected new frames 56 do not cause the lenses to directly contact the cheeks of the user 10.

Once the position of the new frames 56 relative to the user's pupil height is known, the other anatomical variables listed in Table 1 can be calculated. This includes overall pantoscopic tilt angle "PTA" and rear vertex distance "RVD".

Once all of the variables listed in Table A are calculated for the selected new frames 56, the prescription lenses for those new frames 56 are fabricated. See Block 82. The proper adjustments are made to the nose pads and to the temples. The result is a custom fit set of prescription eyewear that fits as well as the original frames fitted by the optician. The online retailer 58 then delivers the new fitted prescription eyewear to the user 10. See Block 84.

It will be understood that the exemplary embodiment of the present invention system that is illustrated is merely exemplary and that many aspects of the system can be redesigned in manners that are functionally equivalent. All such variations, modifications and alternate embodiments are intended to be included within the scope of the present invention as claimed.

What is claimed is:

1. A method of obtaining measurements needed to correctly fabricate prescription eyewear for an individual that requires lenses made according to fitting measurement data, said method comprising the steps of:
   providing an initial set of frames, wherein said initial set of frames have a first datum line and a first set of nose contact points;
   fitting said initial set of frames to the individual to obtain fitted frames, wherein said first set of nose contact points are positioned at a first nose contact point level that is a first distance from said datum line, and wherein said first distance is part of said fitting measurement data needed to fabricate said lenses for said fitted frames;
   imaging said fitted frames while being worn by the individual, therein creating reference images;
   selecting a subsequent set of frames, wherein said subsequent set of frames have a second datum line and a second set of nose contact points;
   obtaining fitting measurements from said reference images;
   utilizing said fitting measurements to fit said subsequent set of frames to the individual wherein, when fitted, said second set of nose contact points are positioned at a second nose contact point level that is a second distance from said second datum line;
   comparing said first distance with said second distance to obtain a differential in position; and
   utilizing said differential in position to alter said fitting measurement data, therein obtaining altered fitting measurement data; and
   utilizing said altered fitting measurement data to form said lenses for said subsequent set of frames.

2. The method according to claim 1, further including storing said reference images and said fitting measurement data on a database that is remotely accessible through a data network.

3. The method according to claim 1, wherein imaging said fitted frames while being worn by the individual includes taking a forward facing image of the individual wearing said fitted frames and at least one alternate angled image of the individual wearing said fitted frames.

4. The method according to claim 1, wherein selecting a subsequent set of frames includes remotely selecting said subsequent set of frames online from an online retailer.

5. A method of obtaining measurements needed to correctly fabricate prescription eyewear for an individual, said method comprising the steps of:
   fitting an initial set of frames to the individual wherein said initial set of frames have a first datum line and a first set of nose contact points where said initial set of frames contact the individual, said first set of nose contact points being at a level on said initial set of frames that is a first distance from said first datum line;
   imaging said individual wearing said initial set of frames, therein creating reference images;
   selecting a subsequent set of frames from an online retailer wherein said subsequent set of frames have a second datum line and a second set of nose contact points, wherein said online retailer fits said subsequent set of frames to the individual utilizing fitting measurements obtained from said reference images, wherein said second set of nose contact points contact the individual at a second distance from said second datum line;
   comparing said first distance with said second distance to obtain a differential in position; and
   adjusting said second set of nose contact points to minimize said differential in position.

6. The method according to claim 5, further including performing an eye exam for the individual to generate fitting measurement data for use with said initial set of frames.

7. The method according to claim 6, further including utilizing said differential in position to alter said fitting measurement data for use on said subsequent set of frames.

8. The method according to claim 6, further including storing said reference images and said fitting measurement data on a database that is remotely accessible through a data network.

9. The method according to claim 5, wherein said fitting measurement data include measurements for pupil height, pantoscopic tilt angle, and rear vertex distance.

10. The method according to claim 5, wherein imaging said individual wearing said initial set of frames includes taking a forward facing image of the individual wearing said initial set of frames and at least one alternate angled image of the individual wearing said initial set of frames.

* * * * *